(12) United States Patent
Bak et al.

(10) Patent No.: US 8,921,674 B2
(45) Date of Patent: Dec. 30, 2014

(54) *GUZMANIA* HYBRID NAMED 'ACE'

(71) Applicant: Corn. Bak B.V., Assendelft (NL)

(72) Inventors: Elly Bak, Rijsenhout (NL); Nicholaas D. M. Steur, Oude Niedorp (NL)

(73) Assignee: Corn.Bak B.V., Assebdelft (NL)

( * ) Notice: Subject to any disclaimer, the term of this patent is extended or adjusted under 35 U.S.C. 154(b) by 18 days.

(21) Appl. No.: 13/777,570

(22) Filed: Feb. 26, 2013

(65) Prior Publication Data

US 2014/0245469 A1  Aug. 28, 2014

(51) Int. Cl.
A01H 5/00 (2006.01)
A01H 5/10 (2006.01)
A01H 5/02 (2006.01)
A01H 1/02 (2006.01)

(52) U.S. Cl.
CPC ... *A01H 5/02* (2013.01); *A01H 1/02* (2013.01)
USPC ............................ 800/323; 800/298; Plt./371

(58) Field of Classification Search
USPC ............................................... Plt./371
See application file for complete search history.

(56) References Cited

U.S. PATENT DOCUMENTS

PP9,426 P * 1/1996 Bak et al. ............... Plt./371

OTHER PUBLICATIONS

Print-out of applicaiton number and publication date from Community Plant Variety Office (CPVO) website for corresponding CPVO application No. 2012/1102 filed May 21, 2012 (1 page).

* cited by examiner

*Primary Examiner* — David H Kruse
(74) *Attorney, Agent, or Firm* — Foley & Lardner LLP

(57) ABSTRACT

A new and distinct *Guzmania* hybrid named 'ACE' characterized by solid growth habit; funnel-form rosette plant, measuring about 40 to 50 cm in height (above the pot when flowering); numerous, green color foliage (measuring about 20-50 cm length and about 2.5-5.5 cm in width). Superior floral bract production; bracts are purple in color (closest to RHS 187B); head inflorescence, measuring about 10 cm in height when flowering commences to about 18 cm in height at maturity, and about 12 cm in diameter; and long-lasting habit.

3 Claims, 2 Drawing Sheets
(2 of 2 Drawing Sheet(s) Filed in Color)

GUZMANIA HYBRID NAMED 'ACE'

FIELD OF THE INVENTION

The present invention relates to a new, distinct and stable hybrid of *Guzmania* hybrid, hereinafter referred to as 'ACE'. The present invention relates to seeds which are the *Guzmania* hybrid 'ACE', as well as, plants and plant parts produced by these seeds which have all of the morphological and physiological characteristics of the *Guzmania* hybrid 'ACE'. The present invention also relates to methods for producing these seeds and plants of the *Guzmania* hybrid 'ACE'. Furthermore, the present invention relates to a method of producing progeny *Guzmania* plants by crossing *Guzmania* 'ACE', as either the female or seed or male or pollen parent, with another *Guzmania* plant and selecting progeny.

BACKGROUND OF THE INVENTION

The present invention relates to a new, distinct and stable hybrid of *Guzmania* hybrid, and hereinafter referred to by the variety denomination 'Ace'. The new *Guzmania* 'ACE' originated from a cross made in a controlled breeding program by the inventors in 2005, and then first flowered in 2008, in Assendelft, The Netherlands. The female or seed parent is the *Guzmania lingulata* inbred line identified by code 05295379 (unpatented). The male or pollen parent is the *Guzmania conifera* inbred line identified by code 0529578 (unpatented).

*Guzmania* is a member of the Bromeliaceae family. *Guzmania* is predominantly epiphytic with a few terrestrial species and is native to the tropics. For the most part, species vary in diameter from 7 or 8 inches to 3 or 4 feet and have rosettes of glossy, smooth-edged leaves.

Floral bracts of *Guzmania* frequently have brilliant colors and may last for many months. The range of colors for *Guzmania* is generally from yellow through orange but may also include flame red and red-purple. White or yellow, tubular, three-petalled flowers may also appear on a stem or within the leaf rosette but are usually short-lived.

*Guzmania* may be advantageously grown as pot plants for greenhouse or home use. Typically, the plants are shaded from direct sunlight. During the spring to autumn period, the central vase-like part of the leaf rosette is normally filled with water.

*Guzmania* is native to tropical America. Leaves of *Guzmania* are usually formed as basal rosettes which are stiff and entire and in several vertical ranks. *Guzmania* plants have terminal spikes or panicles which are often bracted with petals united in a tube about as long as the calyx. The ovary is superior and the seeds plumose.

Asexual propagation of *Guzmania* is frequently performed by vegetative means through the use of tissue culture practices. Propagation of *Guzmania* can also be from offshoots which can be detached from the mother plant and grown in an appropriate soil or hark mixture.

Methods for cultivation and crossing of *Guzmania* are well known. For a detailed discussion, reference is made to the following publications, which are incorporated herein by reference: Benzing, David H., THE BIOLOGY OF THE BROMELIADS, Mad River Press, Inc., Eureka (1980); Zimmer, Karl, BROMELIEN, Verlag, Paul Parey, Berlin (1986); and Rauh, Werner, BROMELIEN, Verlag Eugen Ulmer, Stuttgart (1981).

A *Guzmania* inbred is produced by brother/sister crossing over several generations to produce a genetically homozygous plant selection. A hybrid cultivar is produced by crossing two genetically distinct inbred lines, collecting seeds produced by the cross, and germinating seeds so-produced to make hybrid plants. The hybrid seeds and plants produced by this method are uniform with respect their morphological and physiological characteristics.

A need exists for a greater variety of *Guzmania* cultivars with attractive ornamental features. Additionally, a need exists for additional *Guzmania* hybrid cultivars that can be easily propagated by seed. The new *Guzmania* 'ACE' was developed through a controlled breeding program and exhibits unique, desirable and stable characteristics.

SUMMARY OF THE INVENTION

The present invention provides *Guzmania* plant selections that are solid, medium-sized, long-lasting hybrids with superior bract production and red-purple inflorescence that exhibits good keeping quality. The present invention also provides *Guzmania* plant selections with a head inflorescence with a unique red-purple color which distinguishes the new cultivar from typical *Guzmania*.

These and other objectives have been achieved in accordance with the present invention which provides 'ACE' as a new *Guzmania* cultivar that is a product of a planned breeding program conducted by the inventors, Elly Bak and Nico D. M. Steur, in Assendelft, The Netherlands, in 2005. The female or seed parent is the *Guzmania lingulata* inbred line identified by code 05295379 (unpatented). The male or pollen parent is the *Guzmania* conifera inbred line identified by code 0529578 (unpatented).

Both parental cultivars have a sufficient degree of homozygosity such that the progeny of the cross are genetypically and phenotypically uniform. The new hybrid 'ACE' therefore can be produced by sexual reproduction by crossing the parental inbred lines identified by the codes 05295379 and U.S. Pat. No. 0,529,578 to produce a population of progeny plants, each of which has the combination of characteristics as herein disclosed for the new hybrid 'ACE'.

Seeds which are the hybrid 'ACE' are produced by crossing the parental inbred lines identified by the codes 05295379 and 0529578, and are deposited with the American Type Culture Collection, 10801 University Boulevard, Manassas, Va. 20110-2209. ATCC Patent Deposit Designation No. PTA-13108. 2500 seeds were deposited with the ATCC on Aug. 1, 2012 and found viable on Sep. 12, 2012.

OBJECTS OF THE INVENTION

The present invention relates to seeds which produce *Guzmania* hybrid 'ACE'. The present invention also relates to *Guzmania* plants, and parts thereof, having all the physiological and morphological characteristics of *Guzmania* hybrid 'ACE'. The present invention relates to a plant produced from seeds which are *Guzmania* hybrid 'ACE'. The present invention also relates to plant parts, such as pollen, seeds or inflorescence produced by *Guzmania* hybrid 'ACE'.

The present invention relates to a method of producing seed which are *Guzmania* hybrid 'ACE', by a crossing *Guzmania lingulata* inbred line identified by code 05295379 (unpatented) as the female or seed parent with *Guzmania conifera* inbred line identified by code 0529578 (unpatented) as the male or pollen parent. harvesting seeds produced from said cross.

The present invention also relates to a method of producing plants having all the physiological and morphological characteristics of the *Guzmania* hybrid 'ACE' comprising the steps of (a) crossing *Guzmania lingulata* inbred identified by code 05295379 (unpatented) as a female or seed parent with

*Guzmania conifera* inbred line identified by code 0529578 (unpatented) as the male or pollen parent. (b) harvesting seeds produced from said cross; and (c) producing plants from said harvested seeds.

The present invention also relates to producing progeny plants from the cross of *Guzmania* hybrid 'ACE', as the female or male parent, with another *Guzmania* plant, and selecting progeny plants from this cross.

BRIEF DESCRIPTION OF THE PHOTOGRAPHS

The patent or application file contains at least one drawing executed in color. Copies of this patent or patent application publication with color drawings will be provided by the Office upon request and payment of the necessary fees.

The accompanying photographs illustrate the overall appearance of the new *Guzmania* hybrid 'ACE' showing the colors as true as is reasonably possible with colored reproductions of this type. Colors in the photographs may differ slightly from the color values cited in the detailed botanical description which accurately describes the color of 'ACE'.

DETAILED BOTANICAL DESCRIPTION

Figure 1:
FIG. 1 shows a side view perspective of the primary and top bracts produced by a typical potted, flowering plant of 'ACE', at 16 months of age from potting size.
Figure 2:
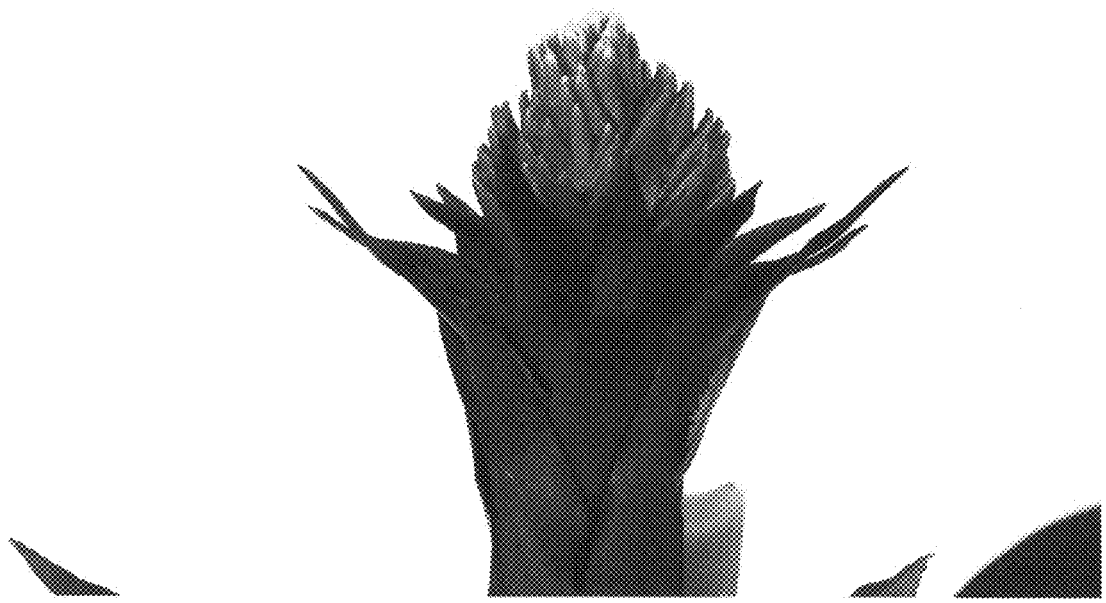
FIG. 2 shows a close-up top view perspective of the inflorescence and top bracts produced by a typical potted, flowering plant of 'ACE', at 16 months of age from potting size.

The present invention was created by the inventors, Elly Bak and Nicolaas D. M. Steur in 2005, and flowered for the first time in 2008 in Assendelft, The Netherlands.

This invention is directed to *Guzmania* plant having all the morphological and physiological characteristics of the hybrid 'ACE' produced from seeds which are the product of the cross of the *Guzmania lingulata* inbred line identified by code 05295379 (unpatented) as the female or seed parent with the *Guzmania conifera* inbred line identified by code 0529578 (unpatented) as the male or pollen parent. Both parents have a sufficient degree of homozygosity such that the progeny of the cross were, and continue to be, phenotypically uniform. The new hybrid 'ACE' can therefore be produced by sexual reproduction by crossing of the inbred selections identified by the codes 05295379 and U.S. Pat. No. 0,529,578 to produce a population of progeny plants, each of which has the combination of characteristics herein disclosed for the new hybrid 'ACE'.

The new hybrid 'ACE' can also be produced by asexually reproducing progeny from the cross of the parental inbred lines identified by the codes 05295379 and 0529578. Asexual reproduction of the new cultivar by vegetative means by cuttings was first performed in 2008, in Assendelft, The Netherlands. The first 'ACE' plants propagated through the use of such cuttings flowered in 2011, in Assendelft, The Netherlands, and have demonstrated that the new cultivar reproduces true-to-type and that the combination of characteristics as herein disclosed for the new cultivar are firmly fixed and retained through successive generations of asexual reproduction.

BRIEF DESCRIPTION OF THE INVENTION

The following traits have been repeatedly observed and are determined to be unique characteristics of 'ACE' which in combination distinguish this *Guzmania* as a new and distinct cultivar:

1. Solid growth habit;
2. Funnel-form rosette plant, measuring about 40 to 50 cm in height (above the pot when flowering);
3. Numerous, green color foliage (measuring about 20 cm to 50 cm in length and about 2.5 cm to 5.5 cm in width.
4. Superior floral bract production;
5. Bracts are purple in color (closest to RHS 187B)
6. Head inflorescence, measuring from about 10 cm in height when flowering commences and about 18 cm in height at maturity, and about 12 cm in diameter
7. Long-lasting habit.

Of the many commercial cultivars known to the present inventors, the most similar in comparison to the new *Guzmania* hybrid 'ACE' is the *Guzmania* cultivar 'ALTO' (patented, US PP21,215). Plants of the new hybrid 'ACE' differ from plants of 'ALTO' primarily in inflorescence size. Plants of 'ACE' produce inflorescence which are 70 cm in diameter whereas plants of 'ALTO' produce inflorescence which are 60 cm in diameter.

'ACE' has not been tested and observed under all possible environmental conditions. The phenotype of the new cultivar may vary with variations in environment such as temperature, light intensity, frequency of fertilization, composition of fertilizer, acetylene treatment, day length and humidity, without any change in the genotype of the plant.

For example, substantial differences in plant height and diameter, number of leaves, can result depending on the size of the plant at the time that flowering is induced by flowering treatment. Since treatment to induce flowering disrupts normal watering and fertilization regimens. flowering treatment of relatively smaller plants adversely affects the growth of the plant.

The aforementioned photographs, together with the following observations, measurements and values describe the new *Guzmania* 'ACE' as grown in a greenhouse in Assendelft, The Netherlands, under conditions which closely approximate those generally used in commercial practice. Plants of 'ACE' were grown in a greenhouse with day temperatures ranging from 20° C. to 28° C. and night temperatures ranging from 18° C. to 23° C. No artificial lighting or photoperiodic treatments were conducted, but plants of 'ACE' are forced into flowering. The following fertilizer is added when growing plants of 'ACE': I part nitrogen, 0.6 parts phosphor, 2 parts Kalium and 0.1 parts magnesium.

Color references are made to the Royal Horticultural Society Colour Chart (RHS), 2001 edition, except where general colors of ordinary significance are used. Color values were taken under daylight conditions in a greenhouse in Assendelft, The Netherlands. The age of the plants of 'ACE' described is about 18 weeks after flowering treatment.

Classification:
Botanical: *Guzmania* sp.
Parentage:
Female Parent: *Guzmania lingulata* inbred line identified by code 05295379 (unpatented)
Male Parent: *Guzmania conifera* inbred line identified by code 0529578 (unpatented)
Plant:
General Appearance and Form:
  Height: About 44 cm (when flowering)
  Width: About 70 cm
  Shape: Funnel form rosette
  Growth habit: Stemless
  Plant Vigor: Good Flowering Season: A fully grown plant can flower year round, starting 18 to 20 weeks after induction of natural light or through flowering treatment.
Cold Tolerance: Frost tender. Temperatures below 5° C. may damage plants.
Fragrance: None
Foliage:
Quantity: About 20-26 (depending on the size of the plant)
Size of Leaf:
  Length: About 20 cm to 50 cm (when flowering)
  Width: About 2.5 to 5.5 cm
Overall Shape: Linear-Lanceolate
Apex Shape: acute
Base Shape: strap-like around central axis
Margin: entire
Texture: smooth
Orientation: leaf blades arch continuously from base.
Color: Leaf color can vary somewhat depending on growing conditions.
  Immature and Mature:
    Upper surface: Green, RHS 147A
    Under surface: Green, RHS 147A with anthocyanin
Venation: None
Inflorescence:
Borne: Erect stalks
Shape: head
Size:
  Length: About 10 cm in height when flowering commences and about 18 cm in height at maturity
  Diameter: About 12 cm
Time of Bloom: A fully grown plant can produce an inflorescence containing about 150 flowers (depending on the size of the plants), and can bloom the whole year starting about 18 to 20 weeks after natural induction or through flowering treatment.
Duration of Bloom: Each flower blooms one (1) day and the total blooming of the whole inflorescence is about 20 weeks.
Petals:
  Number: 3 per flower
  Length: About 6 cm
  Width: About 0.8 cm
  Overall Shape: ligulate
  Apex Shape: obtuse
  Base Shape: fused
  Color:
    Upper and under surfaces: Yellow, RHS 9A
Sepals:
  Number: 3 per flower
  Length: About 3 cm
  Width: About 0.5 cm
  Overall Shape: ligulate
  Apex Shape: acute
  Base Shape: fused
  Color:
    Upper and under surfaces: translucent yellow, closest to RHS 9D
Bracts:
Scape Bracts:
  Quantity: About 12
  Arrangement: alternate
  Size:
    Length: About 30 cm (lowest) to about 10 cm (scape bracts positioned just below the primary bracts).
    Width: About 3 cm to 4 cm
  Overall shape: Lanceolate
  Apex shape: acute
  Base shape: fused
  Margin: Entire
  Texture: Smooth
  Color:
    Upper and under surfaces: Green, closest to RHS 147A
Primary Bracts:
  Quantity: About 8
  Arrangement: Alternate
  Size:
    Length: About 10 cm (lowest) to about 7 cm
    Width: About 4 cm
  Overall shape: lanceolate
  Apex shape: acute
  Base shape: fused
  Margin: entire
  Texture: smooth
  Color:
    Upper and under surfaces: purple, closest to RHS 187B
Floral bracts:
  Quantity: about 150
  Size:
    Length: About 7 cm (lowest) to about 2 cm (become shorter closer to top of plant)
    Width: about 1 to 3 cm
  Overall shape: lanceolate
  Apex shape: obtuse
  Base shape: fused
  Margin: entire
  Texture: smooth
  Color:
    Lower floral bracts (closer to bottom of plant): upper and under surfaces: red, RHS 53A
    Higher floral bracts (closer to top of plant): upper and under surfaces: red, RHS 53A, with yellow bract ends, RHS 12A
Reproductive Organs:
Androecium:
  Stamen:
    Number: 6 per flower
    Length: About 4.5 cm
    Diameter: About 1 mm
    Color: Yellow, closest to RHS 5D
  Anther:
    Length: About 0.6 cm
    Color: Yellow, RHS 5D
  Pollen:
    Amount: None
Gynoecium:
  Pistil:
    Number: 1 per flower
    Length: About 5 cm
  Stigma:
    Shape: 3-parted
    Width: About 3 mm
    Color: light green, (too small to distinguish RHS value)
  Style:
    Length: About 4 cm
    Color: light yellow, (too small to distinguish RHS value)
  Ovary:
    Position: Superior
    Shape: Conical
    Length: About 1 cm
    Diameter: About 0.5 cm
    Color: light green, (too small to distinguish RHS value)
SEEDS/FRUIT: sterile hybrid, no seed or fruit produced.
DISEASE/PEST RESISTANCE: No observations made.
DISEASE/PEST SUSCEPTIBILITY: No observations made.

We claim:
1. A *Guzmania* plant named 'ACE', representative seed having been deposited at the American Type Culture Collection (ATCC) with Patent Deposit Designation No.: PTA-13108.
2. A *Guzmania* seed having American Type Culture Collection (ATCC) Patent Deposit Designation No.: PTA-13108.
3. A plant part obtained from the *Guzmania* plant of claim 1.

* * * * *